United States Patent [19]
Giacobbe et al.

[11] 4,188,330
[45] Feb. 12, 1980

[54] SUBSTITUTED PHTHALIDE DERIVATIVES

[75] Inventors: Thomas J. Giacobbe, Concord; Halbert C. White, Clayton, both of Calif.

[73] Assignee: The Dow Chemical Company, Midland, Mich.

[21] Appl. No.: 949,479

[22] Filed: Oct. 10, 1978

[51] Int. Cl.² ............................................. C07D 307/88
[52] U.S. Cl. ........................ 260/343.3 R; 260/325 PH; 424/279
[58] Field of Search ................................ 260/343.3 R

[56] References Cited
U.S. PATENT DOCUMENTS 3,055,904   9/1962   Graf et al. ...................... 260/343.3 R
3,296,276   1/1967   Sherlock et al. ............... 260/343.3 R

OTHER PUBLICATIONS

Graf et al. (II), Helv. Chim. Acta., XLII, p. 1085, 1959.
Graf et al. Chem. Abstracts, vol. 62, 16200c, vol. 58, 9028d, vol. 59, 9901e, vol. 58, 11330h.

Primary Examiner—Natalie Trousof
Assistant Examiner—Jane T. Fan

[57] ABSTRACT

Method of preparing chlorthalidone, an antihypertensive agent, and derivatives using a novel 3-(4'-chloro-3'-chlorosulfonylphenyl)phthalide intermediate and derivatives, and method of preparing said novel intermediate, are disclosed.

3 Claims, No Drawings

SUBSTITUTED PHTHALIDE DERIVATIVES

BACKGROUND OF THE INVENTION

Chlorthalidone, i.e., 1-oxo-3-(3'-sulfamyl-4'-chlorophenyl)-3-hydroxyisoindoline, is a well known antihypertensive agent and is referenced on page 28 of The Merck Index, 9th Edition, 1976. Chlorthalidone and related compounds, hereinafter referred to for convenience as "isoindoline" compounds, and methods of preparation therefore are also disclosed in U.S. Pat. No. 3,055,904. Referring to the preparation of chlorthalidone itself for purposes of illustration, the '904 reference generally teaches that 2-(4'-chlorobenzoyl)benzoic acid (1) (Ind. & Eng. Chem. 369, 1929) is nitrated in the presence of sulfuric acid to form 2-(4'-chloro-3'-nitrophenyl)benzoic acid (2), the nitro group of (2) being subsequently reduced to an amine derivative (e.g., 2-(4'-chloro-3'-aminophenyl)benzoic acid) (3) which is diazotized to form a diazonium halide derivative (4), in turn decomposed in the presence of copper salts and sulfur dioxide to form a 2-(4'-chloro-3'-sulphochlorobenzoyl)-benzoic acid, or 4-chloro-2'-carboxy-benzophenone-3-sulphochloride (5). The latter compound can be treated with thionyl chloride to form the dichloride, i.e., 3-chloro-3-(3'-chlorosulfonyl-4'-chlorophenyl)phthalide (6) which is then treated with form the desired isoindoline compound, in this case, 1-oxo-3-(3'-sulphamyl-4'-chlorophenyl)-3-hydroxyisoindoline.

The above noted procedure does, however, suffer disadvantages in that numerous process steps are required and that a hazardous diazotization step is necessarily employed. A synthesis method which has fewer total steps and which avoids the hazardous diazotization steps would thus be desirable and it is the principal object of the present invention to therefore provide a method which obviates such disadvantages.

SUMMARY OF THE INVENTION

The present invention is directed to novel substituted 3-(4'-halo-3'-sulfonylphenyl)phthalides and related derivatives and a method of preparing the same comprising sulfonating a 3-(4'-halophenyl)phthalide or related derivative with a selected sulfonating agent. The foregoing substituted phthalides are useful as intermediates in the preparation of isoindoline and isoindoline-like materials which have useful pharmacological properties. The use of said novel intermediates provides an isoindoline synthesis method having fewer and potentially less hazardous steps as the preparation of diazonium salt intermediates can be avoided.

DETAILED DESCRIPTION

One embodiment of the present invention is directed to novel substituted 3-(4'-halo-3'-sulfonylphenyl)phthalide and related compounds which correspond to the following formula:

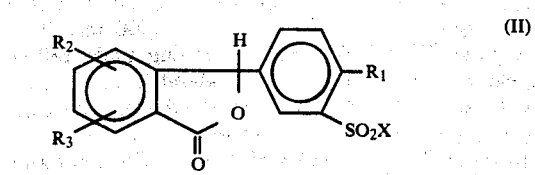

wherein $R_1$ represents chloro, bromo, NR'R", lower alkyl or lower alkoxy radicals, $R_2$ and $R_3$ each independently represent hydrogen, chloro, bromo, nitro or lower alkyl radicals, and X represents chloro, bromo or NR'R" radicals, wherein R' and R" taken separately represent hydrogen, lower alkyl, lower alkenyl or lower hydroxyalkyl radicals. Preferred compounds are those wherein X represents chloro or bromo. Other preferred compounds are those wherein $R_1$ represents chloro or bromo and $R_2$ and $R_3$ each represent hydrogen. Where X is NR'R", one of R' and R" is preferably always hydrogen. An especially preferred compound is one wherein $R_1$ is chloro, $R_2$ and $R_3$ each are hydrogen and X is chloro. As used herein, the terms lower alkyl, lower alkenyl and lower hydroxy alkyl or lower alkoxy are inclusive of carbon chains, straight or branched, of from 1 to about 4 carbon atoms.

The foregoing compounds of Formula II can be prepared according to a second embodiment of the invention, by treating a phthalide reactant of the formula:

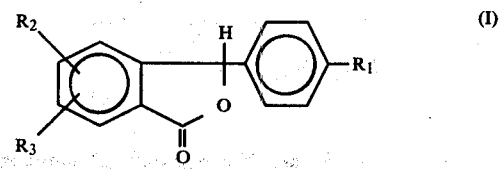

with a sulfonating agent of the formula $XSO_3H$ wherein $R_1$, $R_2$, $R_3$ are as defined above and X is chloro or bromo. The reaction is ordinarily carried out at temperatures of from about 0° to about 120° C., preferably from about 20° to about 70° C., by reacting excess molar amounts of the sulfonating agent with the reactant of Formula I. Typically, excess molar amounts of sulfonating agent, e.g., chloro- or bromo-sulfonic acid:reactant range from about 5:1 to about 100:1. Generally, the reaction mixture is stirred or agitated and the reaction can be carried to substantial completion in a period ranging from about 1 to about 20 or more hours where temperatures of the preferred range are employed. Longer reaction time periods will be required where temperatures in the lower end of the general range are employed. Following substantial completion of the reaction, the course of which can be monitored by determining the amount of HCl liberated, taking aliquots and following by liquid chromatography means, etc., the reaction mixture is added, usually dropwise, to an ice water mixture. The resulting product precipitate is recovered and dissolved in an appropriate solvent, such as chloroform or methylene chloride and the desired product recovered therefrom by adding a non-solvent, reducing the organic mixture to dryness under reduced pressure or until the product precipitates therefrom, etc. Those compounds of Formula II wherein X is NR'R" can be prepared by treating the corresponding halosulfonyl derivative with ammonia or an ammonium derivative according to procedures known in the art, such as is taught in U.S. Pat. No. 3,055,904.

In what is presently believed to constitute the best mode of carrying out the invention as it pertains to the foregoing embodiments, the compounds of Formula II, especially those of the previously noted preferred embodiments, are prepared by reacting a corresponding Formula I reactant with chlorosulfonic acid in a Formula I reactant:chlorosulfonic acid molar ratio of about 1:10 at a temperature of from about 65° to about 75° C. for about 2 to about 3 hours.

In another embodiment of the present invention, isoindoline compounds of the formula:

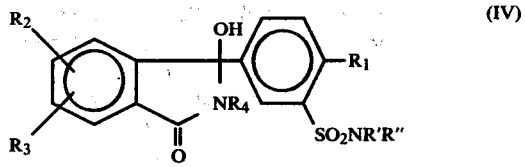

wherein $R_1$, $R_2$, $R_3$, $R'$ and $R''$ are as defined herein above and $R_4$ is hydrogen or lower alkyl are prepared by a method comprising (a) halogenating a compound of Formula II with a halogenating agent to form a corresponding compound of the formula:

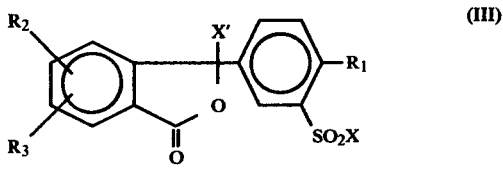

wherein $R_1$, $R_2$, $R_3$ and X are as defined above in Formula II, and $X'$ is a chloro or bromo radical, and (b) treating said compound of Formula III with ammonia or an ammonium derivative to form a corresponding Formula IV isoindoline compound and thereafter recovering said isoindoline compound. Where X in Formula III is chloro or bromo, it will be converted in step (b) to —NR'R''.

Preferred isoindoline compounds of Formula IV include those wherein $R_1$ is chloro or bromo, $R_2$, $R_3$ and $R_4$ are hydrogen. In a most preferred embodiment, $R_1$ is chloro and $R_2$, $R_3$, $R_4$, $R'$ and $R''$ are all hydrogen.

In carrying out the process, compound II, which is prepared as noted hereinabove from compound I, is halogenated with an appropriate halogenating agent which is effective to provide $X'$ in the 3-position, such as, for example, chlorine, bromine, phosphorous pentahalides, combinations thereof such as phosphorous tri- or pentachloride and chlorine gas, and the like. Generally, an inert carrier medium, such as chlorobenzene, toluene or the like, can be employed if desired and the Formula II compound is halogenated with an excess molar amount of halogenating agent. A mole ratio of halogenating agent:Formula II reactant of from about 2–10:1 or higher is usually employed and temperatures of from about 130° to about 150° C. are preferred.

Typical halogenation procedures pertaining to the halogenation of aliphatic carbons known in the art can be employed herein. Preferably, the Formula II phthalide is reacted with the halogenating agent in the presence of an inert carrier medium under reflux conditions for about 2 to about 3 hours. The reaction mixture can be extracted with water, and then concentrated to dryness under reduced pressure to obtain the corresponding Formula III compound. Alternatively, the Formula II reactant is halogenated at temperatures of from about 100° to about 150° C. for about 20–30 minutes, after which time the reaction mixture is quenched with water. The resulting residue extracted with a solvent, such as dichloromethane, and the solvent mixture dried, filtered, diluted with hexane and concentrated by distillation. The thus-obtained 2-(4'-substituted-3'-substituted sulfonyl benzoyl) benzoic acid derivative are then treated with thionyl chloride according to the procedures of U.S. Pat. No. 3,055,904 to give the corresponding Formula III phthalide product.

The thus-formed halogenated compound corresponding to Formula III is then treated in the presence of an inert carrier, such as chloroform or the like, with ammonia or an ammonium derivative according to known procedures. Typically, a mixture of 200 parts of a 25% aqueous ammonia solution and 200 parts of ethanol, methanol, ethylene glycol or the like are employed, the addition thereof usually being carried out portionwise. The desired isoindoline compound can be recovered from the reaction mixture by distilling off the solvent and then acidifying the same with dilute HCl to precipitate the same.

The best mode for carrying out this embodiment of the present invention is believed to be represented by the preparation of the preferred chlorthalidone compound, e.g., 1-oxo-3-(3'-sulfamyl-4'-chlorophenyl)-3-hydroxyisoindoline, by halogenating 3-(4'-chloro-3'-chlorosulfonylphenyl)phthalide (II) with about a tenfold molar excess of phosphorous pentachloride in the presence of chlorobenzene at a temperature of from about 125° to about 135° C. over a period of about 2 hours, and subsequently mixing the thus-formed 3-chloro-3-(4'-chloro-3'-chlorosulfonylphenyl)phthalide (III) with chloroform and treating the resulting mixture with a solution of 200 parts of 25% aqueous ammonia and 200 parts of ethanol, the same being added dropwise at about 10° while stirring and cooling the reaction mixture, then subsequently acidifying the reaction mixture with dilute HCl to precipitate the desired product therefrom. The method described avoids the disadvantages of the prior art methods employing diazotization steps and can be carried out with fewer steps.

The starting materials of Formula I are known in the art and can be prepared by known methods, or by using known reducing agents, such as boron hydrides. See, for example, Rec. Trav. Chim. 82, 801–805 (1962). The starting materials and methods used to prepare I are also known in the art and can be readily prepared by the same or analagous methods; see, for example, U.S. Pat. No. 3,055,904; Ind. and Eng. Chem., 369 (1929), etc.

The following examples illustrate the present invention and the manner by which it can be practiced but, as such, are not to be construed as limitations upon the overall scope of the same.

EXAMPLES

EXAMPLE 1

3(4'-Chlorophenyl)phthalide

A five-liter, 3-neck flask fitted with a reflux condensor and drying tube, an air-driven stirring blade, and thermometer and temperature controller was charged with 2-(4'-chlorobenzoyl)benzoic acid (130.3 grams; 0.5 mol), zinc dust (490.3 g; 7.5 gram-atom), glacial acetic acid (2500 milliliters (ml)), and water (500 ml). The resulting mixture was heated, with stirring, under reflux temperatures (about 105° C.) for about 2 hours. The acetic acid solution was then decanted from the zinc and poured into 4 liters of cold water and the resulting white, fluffy needles were collected by filtration and dried at 60° C. at 10 mm of pressure for 14 hours. As a result of such operations, the desired 3-(4'-chlorophenyl)phthalide compound of Formula I was obtained in a yield of about 88%. Recrystallization from ethanol gave a purified product having an m.p. of 123.5°–124°

C. as compared to a literature reference (*Rec. Trav. Chim.*, 82, 801–805 (1963)) of 122°–125° C.

EXAMPLE 2

3-(4'-Chloro-3'-chlorosulfonylphenyl)phthalide

A three-liter, 3-neck flask equipped with a condensor and drying tube, magnetic spin-bar, thermometer and temperature controller was charged with 48.9 grams (0.2 mol) of the 3-(4'-chlorophenyl)phthalide of Example 1 and with chlorosulfonic acid (1467 ml—about 30 ml/gram of reactant). The resulting dark-purple mixture was stirred and heated at about 70° C. for about 2½ hours. The mixture was subsequently added, dropwise, over a period of about 2½ hours, to a stirred ice-water mixture in order to decompose the chlorosulfonic acid. 3 Kg of ice were initially present in the mixture, and an additional 9.5 Kg of ice were added during the dropwise addition. The solid precipitate formed was recovered by filtration, dissolved in dichloromethane (1000 ml), the solution dried over $Na_2SO_4$, filtered, diluted with hexane and concentrated by distillation until buff-colored crystalline needles began to appear. The crystalline solid was recovered by filtration, washed with hexane and dried. As a result of these operations, the desired title compound having an m.p. of 158°–159° C. was recovered in a yield of about 84%.

Analysis Calc'd for: $C_{14}H_8Cl_2O_4S$: C, 48.99; H, 2.35; Cl, 20.66; S, 9.34. Found: C, 49.0; H, 2.59; Cl, 20.42; S, 9.22.

Confirmation that the chlorosulfonation occurred at the 3'-ring position was obtained by photolytically chlorinating and then hydrolyzing the product to 2-(3',4'-dichlorobenzoyl)benzoic acid (a known compound having an m.p. of 185°–187° C.). The m.p. of the product obtained was 185°–186° C., thus confirming the chlorosulfonation in the 3'-ring position. Had the chlorosulfonation occurred in the 2'-ring position, another known compound, 2(2',4'-dichlorobenzoyl)benzoic acid, having an m.p. of 100°–101° C. would have been obtained.

EXAMPLE 3

3-Chloro-3-(4'-chloro-3'-chlorosulphonylphenyl)phthalide

Glass ampoules (12"×1") were charged with 3-(4'-chloro-3'-chlorosulfonylphenyl)phthalide (0.2 gram), phosphorous pentachloride (2.0 grams) with the void space in the ampoules being charged with $Cl_2$ gas (about 30 ml), and the ampoules sealed. The sealed ampoules were heated in an oil bath at about 150°–155° C. for about 20 minutes, removed, and the reaction mixture quenched with about 10 ml of water. The residue or product precipitate was extracted with dichlormethane, and this solution was dried ($Na_2SO_4$), filtered, diluted with hexane and concentrated by distillation until crystals appeared. These crystals were collected by filtration from the cooled solution to give 2-(4'-chloro-3'-chlorosulfonylbenzoyl)benzoic acid (58% yield, m.p. 176°–177° C.) which was converted by treatment with thionyl chloride to the title compound using the procedure described in U.S. Pat. No. 3,055,904.

In a preferred procedure, 3-(4'-chloro-3'-chlorosulfonylphenyl)phthalide (17.15 g) and phosphorous pentachloride (104 g.) is heated under reflux for 2.5 hours in 300 ml of chlorobenzene. The cooled solution is extracted three times with 100 ml portions of water, dried ($Na_2SO_4$), filtered, and concentrated under a reduced pressure to give a yellow oil from which the title compound can be fractionally crystallized.

The thus-obtained product is readily converted to the desired 1-oxo-3-(3'-sulfamyl-4'-chlorophenyl)-3-hydroxyisoindoline, e.g., chlorthalidone, by treatment with ammonia or an ammonium derivative according to known procedures, such as are taught in U.S. Pat. No. 3,055,904.

Utilizing the foregoing procedures noted in the specification and illustrated in the examples, other desired products ocrresponding to Formulas II and IV herein can be readily prepared.

What is claimed is:

1. A compound of the formula

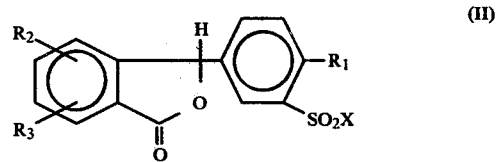

(II)

wherein $R_1$ represents chloro, bromo, NR'R", lower alkyl or lower alkoxy radicals, $R_2$ and $R_3$ each independently represent hydrogen, chloro, bromo, nitro or lower alkyl radicals, and X represents chloro or bromo, R' and R" each independently representing hydrogen, lower alkyl, lower alkenyl or lower hydroxyalkyl radicals.

2. The compound of claim 1 wherein $R_1$ represents bromo or chloro, $R_2$ and $R_3$ each represent hydrogen and X represents chloro or bromo.

3. The compound of claim 2 wherein $R_1$ and X are each chloro.

* * * * *